United States Patent
Koshti et al.

(10) Patent No.: US 10,259,774 B1
(45) Date of Patent: Apr. 16, 2019

(54) ANTIMICROBIALS FOR PRESERVATION OF HOME AND PERSONAL CARE PRODUCTS

(71) Applicant: GALAXY SURFACTANTS LTD., Navi Mumbai (IN)

(72) Inventors: Nirmal Koshti, Piscataway, NJ (US); Pritesh Mhatre, Raigad (IN); Shraddha Ratnaparkhe, Thane (IN); Sneha Ghadigaonkar, Thane (IN)

(73) Assignee: GALAXY SURFACTANTS LTD., Pawne (IN)

( * ) Notice: Subject to any disclaimer, the term of this patent is extended or adjusted under 35 U.S.C. 154(b) by 0 days.

(21) Appl. No.: 15/892,125

(22) Filed: Feb. 8, 2018

(51) Int. Cl.
| | | |
|---|---|---|
| *A61K 8/41* | (2006.01) | |
| *A61K 8/64* | (2006.01) | |
| *A61K 8/67* | (2006.01) | |
| *C11D 1/02* | (2006.01) | |
| *C11D 1/38* | (2006.01) | |
| *C11D 1/88* | (2006.01) | |
| *C11D 3/00* | (2006.01) | |
| *C11D 3/20* | (2006.01) | |
| *C11D 3/30* | (2006.01) | |
| *C11D 3/32* | (2006.01) | |
| *A61Q 17/00* | (2006.01) | |
| *C07C 209/12* | (2006.01) | |
| *C07C 209/60* | (2006.01) | |
| *C07C 211/63* | (2006.01) | |

(52) U.S. Cl.
CPC ............ *C07C 211/63* (2013.01); *A61K 8/416* (2013.01); *A61K 8/64* (2013.01); *A61K 8/67* (2013.01); *A61Q 17/005* (2013.01); *C07C 209/12* (2013.01); *C07C 209/60* (2013.01); *C11D 1/02* (2013.01); *C11D 1/38* (2013.01); *C11D 1/88* (2013.01); *C11D 3/0089* (2013.01); *C11D 3/2065* (2013.01); *C11D 3/30* (2013.01); *C11D 3/323* (2013.01); *A61K 2800/436* (2013.01); *A61K 2800/596* (2013.01); *A61K 2800/74* (2013.01)

(58) Field of Classification Search
CPC ... C07C 211/63; C07C 209/12; C07C 209/60; A61K 8/416; A61K 8/64; A61K 8/67; A61Q 17/005; C11D 1/02; C11D 1/38; C11D 1/88; C11D 3/0089; C11D 3/2065; C11D 3/30; C11D 3/323
See application file for complete search history.

(56) References Cited

PUBLICATIONS

Shtacher et al., "Synthesis of chelating compounds to be used as potential bone seekers", Journal of Medicinal Chemistry, 9(2), 197-203 (Year: 1966).*

Badreshia, et al., "Iodopropynyl Butylcarbamate", American Journal of Contact Dermatitis, vol. 13, No. 2 Jun. 2002: pp. 77-79.

Curry, et al., "Benzyl Alcohol Allergy: Importance of Patch Testing with Personal Products", Dermatitis, vol. 16, No. 4 Dec. 2005: pp. 203-208.

Degroot, et al., "Isothiazolinone Preservative: Cause of a Continuing Epidemic of Cosmetic Dermatitis", The Lancet, Feb. 11, 1989, pp. 314-316.

Du, "In Vitro Neurotoxicity of Methylisothiazolinone, a Commonly Used Industrial and Household Biocide, Proceeds via a Zinc and Extracellular Signal-Regulated Kinase Mitogen-Activated Protein Kinase-Dependent Pathway", The Journal of Neuroscience, Sep. 1, 2002, 22(17):7408-7416.

Kang, "Decreased Sperm Number and Motile Activity on the F1 Offspring Maternally Exposed to Butyl p-Hydroxybenzoic Acid (Butyl Paraben)", J. Vet. Med. Sci. 64(3): 227-235,2002.

Kumar, et al., "Alteration of testicular steroidogenesis and histopathology of reproductive system in male rats treated with triclosan", Reproductive Toxicology 27 (2009) 177-185.

Pedersen, et al., "The Preservatives Ethyl-, Propyl- and Butylparaben are Oestrogenic in an in vivo Fish Assay", Pharmacology & Toxicology 2000, 86, 110-113.

Schmuck, et al., "2-Phenoxyethanol: a neurotoxicant?", Arch. Toxicol. (2000) 74: 281-283.

Zorrilla, et al., "The Effects of Triclosan on Puberty and Thyroid Hormones in Male Wistar Rats", Toxicological Sciences 107(1), 56-64 (2009).

* cited by examiner

*Primary Examiner* — Pancham Bakshi
*Assistant Examiner* — Mark R Luderer
(74) *Attorney, Agent, or Firm* — Kramer Amado, P.C.

(57) ABSTRACT

Disclosed herein are antimicrobial N-Alkyl-N,N-bis(2-carboxyethyl)-N-benzyl ammonium chlorides of Formula I for preservation of home and personal care products. The invention further discloses a process for preparation of the antimicrobial compounds and home & personal care compositions comprising the N-Alkyl-N,N-bis(2-carboxyethyl)-N-benzyl ammonium chlorides of Formula I Formula I

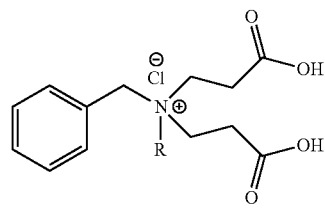

R=$C_{8-18}$ saturated or unsaturated alkyl group.

12 Claims, No Drawings

ANTIMICROBIALS FOR PRESERVATION OF HOME AND PERSONAL CARE PRODUCTS

FIELD OF INVENTION

The present invention relates to broad spectrum antimicrobials for preservation of home and personal care products. More particularly, the present invention relates to antimicrobial N-Alkyl-N,N-bis(2-carboxyethyl)-N-benzyl ammonium chloride compounds, also referred to herein as N-Alkyl, N,N-dipropionic acid, N-benzyl ammonium chlorides; and process for preparation thereof.

These antimicrobial compounds are compatible with anionic surfactants and are good replacement for all the eco-toxic preservatives such as halogenated chemicals (Methylchloroisothiazolinone, Iodopropynyl butyl carbamate, Triclosan, Chlorphenesin, Bronopol), parabens, and formaldehyde releasers (DMDM Hydantoin, diazolidinyl urea and other urea derivatives).

BACKGROUND AND PRIOR ART OF THE INVENTION

Preserving personal care products from microbial degradation is quite challenging. Most topical cosmetics and dermatological products in the form of creams, lotions, gels, shampoos, body-washes and face-washes contain significant amount of water. This provides a very hospitable environment for the microbial growth. In addition to water, other cosmetic ingredients can also be a good source of nutrients to microbes. Another pertinent point to be reckoned here is that the shelf-life of the personal care products and the period after opening the container by the consumer is quite long compared to pharmaceutical products or food products. Unlike pharmaceutical products, cosmetics products are neither sterilized nor packed in hermetic conditions. Thus, the requirement for preservation of the personal care products is, indeed, quite challenging. This is further compounded by the limited choice of antimicrobials since the available approved antimicrobials are very few and those which have good antimicrobial activity are quite toxic. Consumers want products meant for topical applications to be free from toxic antimicrobials that are used as preservatives. Very effective antimicrobials that are used currently, are implicated in serious toxicity issues to human as well as to environment. For example, parabens are implicated in disrupting endocrine system, ultimately linked to breast cancer [(*Pharmacology & Toxicology* (Vol. 86(3), pp 110-13, March 2000, *Toxicology and Applied Pharmacology* (Vol. 153(1), pp. 12-19 (November 1998), *Journal of Veterinary Medical Science* (Vol. 64(3), pp. 227-35 (March 2002, *Journal of Applied Toxicology*, 24 (3): 167-176, (2004)]. Formaldehyde is classified as Category 3 CMR (carcinogenic, mutagenic and reproductive toxic) and hence all formaldehyde releasers are under the cloud. This class includes the work-horse preservatives such as DMDM hydantoin, diazolidinyl urea, imidazolidinyl urea and Quaternary 15.

Another class of very effective antimicrobials is 'isothiazolinones'. Methyl and chloromethyl isothiazolinones have been used in personal care but these are reported to be neurotoxic and skin sensitizers (*Journal of Neuroscience* 22 (17): 7408-7416. *The Lancet*, Volume 333, Issue 8633, Pages 314-316 (1989). Chloromethyl isothiazolinone (generally abbreviated as CIT) is far more toxic and most of the leading personal care products manufacturers have stopped using it.

Halogenated antimicrobials have their own share of toxicity issues. For example, Triclosan, once a popular antimicrobial for hand sanitizers, is being phased out due to its toxicity. It has been implicated in eco-toxicity issues (algae, dolphins). It is reported to be an endocrine disruptor (thyroid function) and is reported to impair cardiac and skeletal muscles. There seems to be special concern for children who are at higher risk of allergies and the immune systems (Toxicological Sciences, 2009, 107 (1): 56-64, Reproductive Toxicology, April 2009, 27(2): 177-185). Companies such as Johnson and Johnson, Proctor & Gamble and Reckitt Benckiser have removed it from their products. Triclosan's eco-toxicity is such a big concern that its usage has been completely banned by the state of Minnesota in the USA. Iodopropynyl butyl carbamate, another halogenated antimicrobial, is a contact allergen (*American Journal of contact dermatitis* 13(2), 77-79 (2002). The presence of iodine in the molecular structure gets it implicated in Goiter and malfunctioning thyroid gland. It is not allowed in Japan and in European Union (EU) and generally, elsewhere, it is allowed only up to 0.02% in leave-on products. Similarly, EU permits usage of methyl dibromo glutaronitrile only up to 0.1% and that too in only rinse-off products. Another brominated molecule is Bronopol, very widely used once upon a time, is banned today in countries like Canada for its application in cosmetics. It is involved in allergic reactions as well as generation of N-nitroso amines that are known to be carcinogenic. The quaternary ammonium compounds (examples are cetyl pyridinium chloride, benzethonium chloride, benzalkonium chloride) exhibit good antimicrobial activity but their utility in personal care industry is limited due to incompatibility with anionic surface active agents. The cationic antimicrobials are completely neutralized by the anionic surface active agents that are present in large excess in home and personal care formulation (8 to 20%).

Thus, most of the antimicrobials with phenolic nature or containing halogen (chlorine, bromine, or iodine) are toxic. Also, the big class of 'formaldehyde releasing antimicrobials' is being phased out due to highly toxic nature of formaldehyde. Examples of this class are DMDM hydantoin, imidazolidinyl urea and diazolidinyl urea.

To avoid the above mentioned toxic antimicrobials, the industry did come up with alternatives antimicrobial preservatives that are largely based on organic acids such as sorbic acid, benzoic acid, dehydroacetic acid, and alcohols such as phenoxyethanol, benzyl alcohol (Cosmetics Directive Annex VI). However, the biggest disadvantage with all organic acids is that they are effective in very narrow pH range of acidic side typically, 3.0 to 6.0. They tend to lose their efficacy fast as the pH approaches the neutral point or above 7.0. Alcoholic antimicrobials like phenoxyethanol and benzyl alcohol are liquids and exert solvent action in formulations and they do have their share of problems in terms of drop in the viscosity of the formulations. In September 2012, French Agency ANSM (Agence nationale de sécurité des médicaments et des produits de santé) which rose concerns about the use of Phenoxyethanol as preservatives for baby care products due to inadequate safety data and demanded that the upper limit for dose be lowered to 0.4% from 1.0% for baby care products meant for children under the age of 3. In 2016 Scientific Community of Consumer Safety (SCCS) finally declared it to be safe up to 1.0% level for cosmetics. However, the concern remains with the manufacturers of personal care products because of Phenoxyethanol's belonging to the dangerous glycol ether family (methyl cellosolve or ethyl cellosolve, phenoxy ethanol is phenyl cellosolve). Phenoxyethanol is also reported to depress the central nervous system (Schmuck G, Steffens W, Bomhard E (July 2000). "*2-Phenoxyethanol: a neurotoxicant?*" *Archives of Toxicology.* 74 (4-5): 281-3) and it may cause vomiting and diarrhea, which can lead to dehydration in infants. There are some baby care products that mention on the label about being free from phenoxyethanol. (Colgate's baby care brand Tom's of Main, moisturizing lotion).

Benzyl alcohol, another antimicrobial, suffers from disadvantage of being allergen causing allergic contact dermatitis reactions (E. J. Curry and E. M. Warshaw, *Dermatitis,* 2005; 16 (4): 203-208) and strong benzaldehyde like aroma puts a limitation on its deployment as antimicrobial across the personal care products.

So in view of the limitations, restrictions and concerns cited above for the majority of antimicrobials, there remains an urgent need to develop a broad spectrum, organoleptically acceptable antimicrobial, non-toxic (non-phenolic, non-halogenated, non-formaldehyde releaser) and compatible with anionic surfactants which are the mainstay of personal care and for home care formulations.

Objectives of the Invention

The objective of the present invention is to synthesize antimicrobial preservatives for home and personal care products that would avoid all known toxic functional groups like phenolic moiety, formaldehyde releasing functionality or halogens (chlorine, bromine, iodine) and that would be bio-degradable.

Another objective of the present invention is to create a broad spectrum antimicrobial preservative that is compatible with anionic surfactants for personal care and home care products.

Another objective of the present invention is to create antimicrobial preservative for personal care that would be effective in broad pH range covering both acidic and alkaline side.

Yet another objective of the present invention is to create an antifungal preservative that would be effective in anionic surfactant systems at alkaline pH.

SUMMARY OF THE INVENTION

In line with the above objectives, the present invention provides antimicrobial preservatives, N-Alkyl, N,N-dipropionic acid, N-benzyl ammonium chlorides as depicted by Formula I, where R is selected from $C_8$ to $C_{18}$ saturated or unsaturated alkyl chains, for home and personal care products. These compounds of Formula I are effective in the presence of anionic surfactants and over broad pH range covering acidic as well as alkaline range of personal care products.

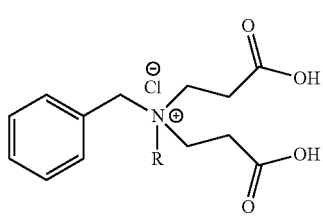

Formula I

In another aspect, the present invention is directed to synthesis of antimicrobial compounds, N-Alkyl, N,N-dipropionic acid, N-benzyl ammonium chlorides, as depicted by Formula I, where R is selected from $C_8$ to $C_{18}$ saturated or unsaturated alkyl chains; the said synthesis comprising the steps of;

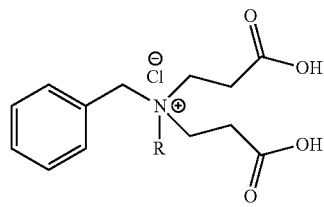

Formula I a) reaction of primary alkyl amine $RNH_2$ with a lower alkyl acrylate ester, e.g., ethyl acrylate or methyl acrylate, to form a Michael adduct (Formula II; $R_1$ is lower alkyl);

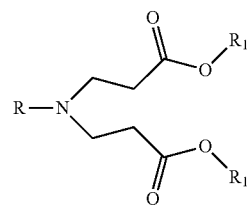

Formula II b) quaternization of Michael adducts (Formula II) of step (a) with benzyl chloride to get compounds of Formula III; and

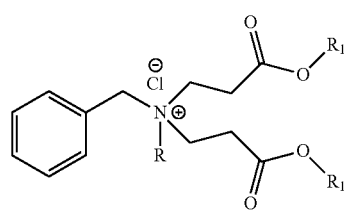

Formula III c) alkaline hydrolysis of quaternized products (Formula III) of step (b) followed by acidification, separation and drying to get the compounds of Formula I. If ethyl acrylate or methyl acrylate are used in step (a), $R_1$ will be ethyl or methyl, respectively.

In another process variant, the compounds of formula I can be prepared by a process which comprises;

a) reacting benzyl amine with a lower alkyl acrylate ester, e.g., ethyl acrylate or methyl acrylate, to obtain a Michael adduct of formula II, wherein R1 is lower alkyl;

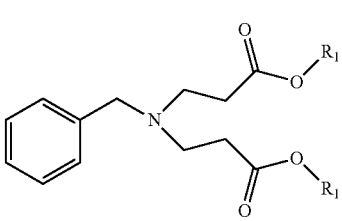

Formula II b) quaternizing the Michael adduct of formula II with a long chain, e.g., C8 to C18, saturated or unsaturated alkyl halide to obtain the compounds of Formula III, wherein R1 is lower alkyl; and

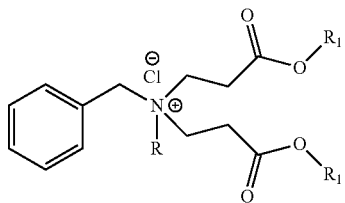

Formula III c) hydrolyzing the compounds of Formula III with alkali and acidification followed by isolation to obtain compound of formula I. If ethyl acrylate or methyl acrylate are used in step (a), $R_1$ will be ethyl or methyl, respectively.

In another aspect, the present invention is directed to preservation efficacy of personal care and home care compositions using the compounds of Formula I.

The benefits and advantages of the present disclosures will be appreciated and understood by those with ordinary skilled in the art, from the following detailed description and the claims.

DETAILED DESCRIPTION OF THE INVENTION

As discussed in the background section that all powerful antimicrobials that are used for preservation of home and personal care products are reported to be toxic to environment. Industry is phasing out the toxic antimicrobial preservatives such as chloromethyl isothiazolinone, Triclosan, parabens, DMDM Hydantoin, and Quaternium 15. In view of this constraint, the personal care industry is trying to use combinations of mild antimicrobials such as phenoxyethanol, benzyl alcohol, dehydroacetic acid and benzoic acid to address the preservation of home and personal care formulations that invariably contain significant amount of water. Often times the combinations of two to six antimicrobials are used to get the desired broad spectrum of activity against Gram negative bacteria, Gram positive bacteria, yeast and mold.

Nearly all personal care formulations, either for skin care or hair care, contain one or more anionic surfactants as either cleansing agents or as emulsifiers/solubilizers. Shampoos, body-washes, shower gels, face-washes, feminine intimate hygiene-washes, hand washes contain significant % of anionic surfactants. Commonly used anionic surfactants are sodium, potassium or ammonium salts of alkyl ether sulphates, alkyl sulphosuccinates, amino acid based surfactants (sodium N-alkanoyl glycinate, sodium N-alkanoyl taurate, sodium N-alkanoyl sarcosinate, sodium N-alkanoyl glutamate) and sodium O-alkanoyl isethionate. The anionic surfactants that are commonly employed by for home care industry are sodium salts of linear alkyl benzene sulphonate (LABS), sodium lauryl sulphate, sodium alpha olefin sulphonate (AOS). These are commonly used for fabric cleansers, dish-wash liquids, hard surface cleaners, carpet shampoos, pet shampoos etc. The amphoteric surfactants that are commonly used in both home and personal care formulations are cocoamidopropyl betaines and long chain tertiary alkyl amine oxides. Commonly used non-ionic surfactants are fatty alcohol ethoxylates and alkyl polyglucosides. Total surfactant content in personal cleansing formulation as well as home care application can vary from 8.0% to 45%. The water content can vary from 30% to 85% and pH can vary from 3.00 to 8.00. Oil-in-water type cream formulations that are emulsions wherein two immiscible phases (oil and water) are brought together by 1 to 5% of surfactants, mostly anionic and in some cases non-ionic or combination of non-ionic and anionic surfactants.

It is important that the antimicrobial preservative for home and personal care formulations is compatible with surfactant systems. It should not be deactivated by either micellar solubilization or ionic interaction with oppositely charged surfactants.

Surprisingly, it has been found that of N-Alkyl, N,N-dipropionic acid, N-benzyl ammonium chlorides of Formula I, wherein R is selected from C8 to C18 saturated or unsaturated alkyl chains, work very efficiently as antimicrobial preservatives in the presence and excess of surfactants, particularly the anionic surfactants. Therefore, the compounds of formula I can be employed in home and personal care compositions as antimicrobial preservative.

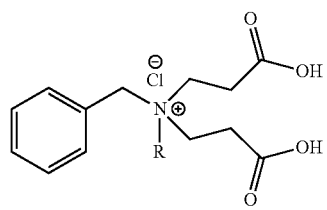

Formula I

According to another embodiment, the synthesis of N-Alkyl, N,N-dipropionic acid, N-benzyl ammonium chlorides of Formula I, wherein R is selected from C8 to C18 saturated or unsaturated alkyl chains, has been achieved as depicted in Scheme 1.

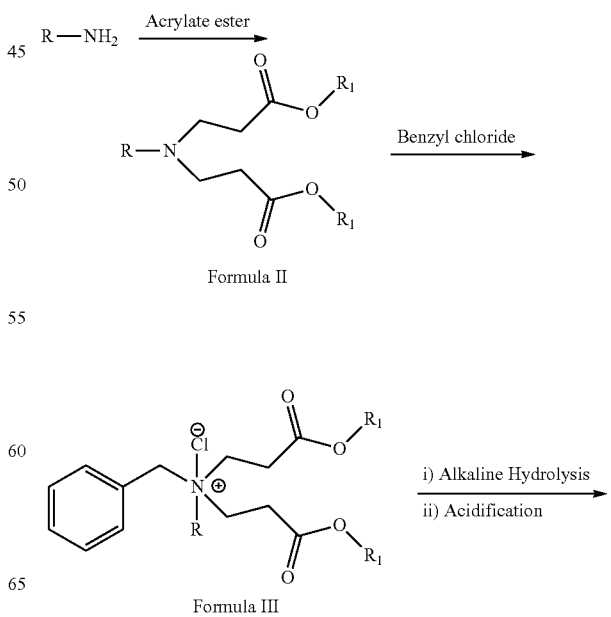

Scheme 1

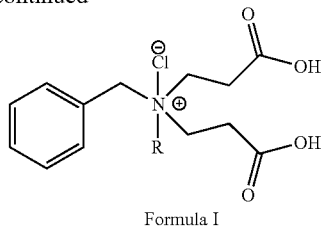

Formula I

Fatty alkyl amines are added to ethyl acrylate or methyl acrylate to give the corresponding Michael adducts of Formula II. The Michael addition is done at room temperature with exact stoichiometry of the reactants required for the formation of the diadducts. The solvent and the traces of unreacted acrylate are removed under vacuum. The diadducts are then dissolved in aqueous isopropanol and quaternized with benzyl chloride by refluxing at 85-90° C. The progress of the reaction is monitored by estimating liberated chloride ion. The quaternized esters (Formula III), thus obtained, are hydrolyzed under alkaline condition and the reaction mass is then acidified and phase separated at 60° C. The phase separated mass is subsequently dried under vacuum to give compounds of Formula I as liquids or low melting waxy solids. The primary fatty alkyl amines used in this patent application range from $C_8$-$C_{18}$ alkyl amines Examples 1, 2, 3 describe the syntheses of compounds of Formula I depicted in Scheme 1 using octyl amine, lauryl amine and oleyl amine.

The alternate route for making compounds of Formula I involves synthesizing Michael adduct of benzyl amine and an acrylate ester and subsequent quaternization by long chain alkyl halide to get the compounds of Formula III (Scheme 2).

Scheme 2

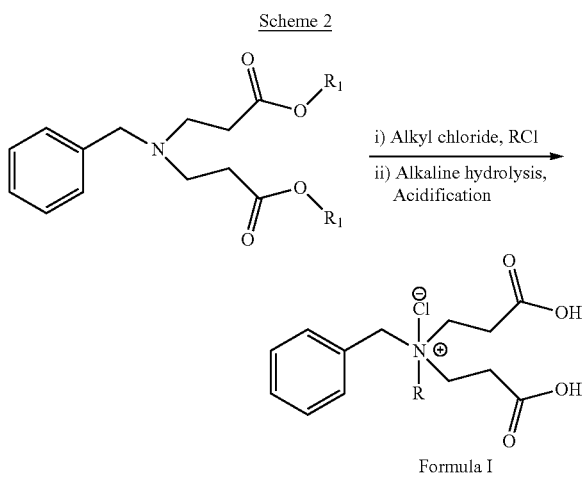

Formula I

The hydrolysis of compounds of Formula III and acidification/isolation steps are the same as described in Scheme 1. The quaternization step of Scheme 1 with benzyl chloride is far more facile than the quaternization step of Scheme 2 with long chain alkyl halide though the latter alternative route of synthesis (Scheme 2) is feasible.

In a further embodiment, the invention provides personal care formulations which comprises N-alkyl, N,N-dipropionic acid, N-benzyl ammonium chlorides of Formula I according to the present invention and one or more ingredients selected from anionic surfactants, amphoteric surfactants, non-ionic surfactants, pearlizers, emollients, anti-inflammatory, anti-microbial preservatives, UV absorbers, UV blockers, synthetic and/or natural polymeric conditioners, silicones, gums, rheology modifiers, vegetable oils, film formers, vitamins, protein derivatives, anti-acne agents, anti-dandruff agents, moisturizers, humectants, botanicals, emulsifiers and other skin and hair actives.

In yet another embodiment, the invention provides home care formulations which comprises N-Alkyl, N,N-dipropionic acid, N-benzyl ammonium chlorides of Formula I according to the present invention and one or more ingredients selected from anionic surfactants, cationic surfactants, amphoteric surfactants, polymers, rheology modifiers, pearlizers, urea, hydrotropes, polyalkylene glycols and chelating agents.

According to a preferred embodiment, the home and personal care formulations comprises at least 0.3% by weight of the total composition of N-Alkyl, N,N-dipropionic acid, N-benzyl ammonium chlorides of Formula I, as an anti-microbial preservative.

Chemistry of N-Alkyl, N,N-Dipropionic Acid, N-Benzyl Ammonium Chlorides (Formula I):

The compounds of Formula I exhibit trend of decreasing water-solubility as the alkyl chain length increases. N-Octyl, N,N-dipropionic acid, N-benzyl ammonium chloride is highly water soluble and so is N-Lauryl, N,N-dipropionic acid, N-benzyl ammonium chloride. They easily form solutions in water with concentrations up to 30% w/w. N-Oleyl, N,N-dipropionic acid, N-benzyl ammonium chloride is dispersible and the dispersions in water are very stable. (Experimental, Example 1, 2, and 3). Also, the physical nature varies as the alkyl chain length increases. Compound of Formula I with octyl chain is a liquid in nature whereas compounds with chain length of $C_{12}$ or higher are low melting solids.

Interestingly, the water-soluble compounds of Formula I, does not reduce the foaming power (Hart de George method, water of hardness 150 ppm) of anionic surfactants very significantly. Foam measurement of 9% solution of Sodium lauryl ether sulphate (Formula VI) gives around 600 ccs of foam. When this SLES (9%) is mixed with 1% N-Lauryl, N,N-dipropionic acid, N-benzyl ammonium chloride then the depression in foam is observed to be 560 cc whereas when SLES (9%) is mixed with 1% benzalkonium chloride (Formula V, N-Alkyl, N,N-dimethyl, N-benzyl ammonium chloride, CAS No 85409-22-9) the foam generation is significantly suppressed (380 cc) compared to 560 cc with compound of Formula I (R=$C_{12}$).

TABLE 1

Foam analysis

| Sample | Appearance | Foam Height (mL) | |
| --- | --- | --- | --- |
| | | pH 6.0 | pH 8.0 |
| Sodium lauryl ether sulphate (SLES) 10% solution | Clear | 600 | 600 |
| 1%, N-Lauryl, N,N-dipropionic acid, N-benzyl ammonium chloride in 9% SLES solution | Clear | 550 | 560 |
| 1%, N-Octyl, N,N-dipropionic acid, N-benzyl ammonium chloride in 9% SLES solution | Clear | 520 | 500 |
| 1% Benzalkonium chloride in 9% SLES solution | Clear | 370 | 380 |

The compounds of Formula I are diacids with a quaternary ammonium center. In acidic condition these behave like cationic surfactant and at alkaline pH, they behave like anionic surfactant. Hence these compounds in a way are amphoteric surfactants.

Just like any other surfactant with an alkyl chain of twelve carbons, the surfactant of Formula I with $R=C_{12}$, N-lauryl, N,N-dipropionic acid, N-benzyl ammonium chloride, foams well and it foams well in acidic conditions unlike the structurally close anionic surfactant sodium lauroyl glycinate with the carboxylate group at the terminal. (Formula IV, CAS no. 18777-32-7).

Formula IV

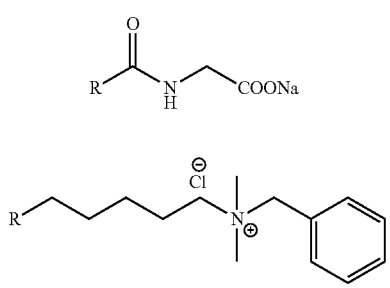

Formula V

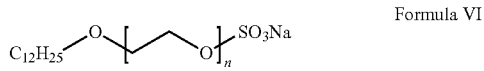

Solution of N-lauryl, N,N-dipropionic acid, N-benzyl ammonium chloride (1% at pH 6.0, Formula I, $R=C_{12}$) foams about the same when compared with 1% solution of sodium lauroyl glycinate at pH 6.0, around 240-250 cc (Formula IV).

Formula VI $C_{12}H_{25}$—O—[—O—]$_n$—SO$_3$Na

The critical micelle concentration (CMC) of N-lauryl, N,N-dipropionic acid, N-benzyl ammonium chloride is 0.3 mmol/L when measured at pH 8.0 whereas at acidic pH of 6.0 CMC was found to be 0.38 mmol/L. This low CMC number shows that it is far milder on skin particularly with respect to its interaction with proteins of corneocytes. CMC of sodium lauryl sulphate is 8.0 mmol/L which is known irritant to skin. Its CMC number is close to other betaine type amphoteric molecules like cocoamidopropyl betaine (CAS no. 61789-40-0) 0.05 mmol/L. The compounds of Formula I of the present patent application, obtained in pure form either in liquid or in the low melting waxy solids, may retain moisture up to 5% maximum. (Experimental, Examples 1, 2, 3). Thus, other than moisture content the rest is all active ingredient as measured by two phase titration against anionic surfactant. (ISO 2871-2: 1990: *Surface active agents-Detergents-Determination of cation-active matter content-Part 2: Cation-active matter of low molecular mass (between 200 and 500)*. International Organization for standardization, Geneva).

Antimicrobial Properties of Compounds of Formula I:

The compounds of Formula I of the present application exhibit good antimicrobial activities. The minimum growth inhibitory concentration numbers (MIC) for N-lauryl, N,N-dipropionic acid, N-benzyl ammonium chloride (Formula I, $R=C_{12}$) and for N-octyl, N,N-dipropionic acid, N-benzyl ammonium chloride (Formula I, $R=C_8$) are given in Table II.

It is interesting to note that the precursors (compounds of Formula III) also exhibit excellent antimicrobial activity as shown in case of methyl ester precursor in Table III.

TABLE II

| Test organism | MIC (%) N-Lauryl, N,N-dipropionic acid, N-benzyl ammonium chloride | MIC (%) N-Octyl, N,N-dipropionic acid, N-benzyl ammonium chloride |
|---|---|---|
| S aureus | 0.5 | 0.2 |
| E coli | 0.7 | 0.2 |
| Pseudomonas sp | 0.4 | 0.5 |
| P acne | 0.6 | 0.5 |
| C. albicans | 0.6 | 0.2 |
| M furfur | 0.5 | 0.2 |
| Aspergillus niger | 0.2 | 0.4 |

TABLE III

| Test organism | MIC (%) N-Lauryl, N,N-dimethyldipropionate, N-benzyl ammonium chloride |
|---|---|
| S aureus | 0.5 |
| E coli | 0.3 |
| Pseudomonas sp | 0.5 |
| P acne | 0.4 |
| C. albicans | 0.4 |
| M furfur | 0.5 |
| Aspergillus niger | 0.2 |

The compounds of Formula III are equally good antimicrobials and their low water solubility compared to the diacids of Formula I, may not hamper their anti-microbial efficacy in aqueous personal care and home care formulations.

Unlike benzalkonium chloride (BKC), the compounds of Formula I do not get deactivated in the presence of anionic surfactants. Thus 10% SLES (Formula VI) when preserved with 1% benzalkonium chloride failed to pass the challenge test whereas 10% SLES with 1 N-lauryl, N,N-dipropionic acid, N-benzyl ammonium chloride of the present invention passes the challenge test as per protocol prescribed by the Personal Care Products Council (PCPC), Washington D.C.

Minimum inhibitory growth concentration of N-lauryl, N,N-dipropionic acid, N-benzyl ammonium chloride against *A. niger* always is found to be in the zone of 0.1 to 0.2%. What is surprising is that the N-lauryl, N,N-dipropionic acid, N-benzyl ammonium chloride exhibits very good antifungal activity against *Aspergillus* in alkaline pH. This is extremely useful discovery since all permitted anti-fungal agents like benzoic acid, sorbic acid and dehydroacetic acid are effective in acidic medium, however, these molecules (organic acids) rapidly lose their antifungal activity as the pH goes toward alkaline side and industry is looking for an effective antifungal agent at alkaline pH. The MIC numbers of compounds of Formula I with respect to *A. niger* have been found to be about the same at pH 6.0 and pH 8.5.

The preservative efficacy of the compounds of Formula I has been tested in surfactant formulations typically containing anionic surfactant with pH ranging for 4 to 8.0. The personal care and home care formulations (body wash, shampoo, skin-cream and dish wash) are preserved with 1.0 to 2.0% of compounds of Formula I. The details of formulations are given in Examples 4, 5, 6, 7, 8, 9, and 10. The above formulations pass the challenge test performed according to PCPC protocol using *Escherichia coli* ATCC 8739, *Pseudomonas aeruginosa* ATCC 15442 (Gram −ve) bacteria), *Staphylococcus aureus* ATCC 6538, *Propionibacterium acnes* MTCC 1951, (Gram +ve) *Candida albicans* ATCC 10231, *Malassezia furfur* MTCC 1374 (yeast) and

*Aspergillus niger* ATCC 16404 (mold) The formulations pass the challenge test criteria for both bacteria and fungi.

However, in the comparative experiment (Experiment 12), the shampoo formulation preserved with 1% Benzalkonium chloride (BKC, Formula V, N-alkyl, N,N-dimethyl, N-benzyl ammonium chlorides, CAS No 8001-54-5) failed the challenge test. Unlike Experiments 4, 5, 6 7, 8, 9 and 10, the formulation (Example 12) preserved with the antimicrobial benzalkonium chloride fails the challenge test. BKC is a cationic antimicrobial and it strongly interacts with anionic surfactants present in the formulation and gets deactivated completely. BKC is a very powerful antimicrobial and its minimum growth inhibitory numbers are between 10 to 200 ppm. (Jon J. Kabara— *Cosmetic and Drug Preservation* p. 732, Publisher name— MARCEL DEKKER, INC. 1984.), however, despite using at 10000 ppm it does not exhibit any antimicrobial activity in the presence of anionic surfactant. The cationic-anionic reaction between sodium laureth sulphate (Formula VI) and benzalkonium chloride (Formula V) also results in significant depression of foaming characteristics of anionic surfactants. There is very small depression of foaming characteristics of an anionic sodium laureth sulphate by equivalent quantity of N-lauryl, N, N-dipropionic acid, N-benzyl ammonium chloride (Table I).

The above examples show that the compounds of Formula I work as 'stand-alone' broad spectrum antimicrobial preservatives. However, the compounds of Formula I are compatible with other preservatives and can be used in combination to create synergistic blends. These can be combined with other antimicrobials like phenoxy ethanol, capryloyl glycine, undecylenoyl glycine, benzoic acid, dehydroacetic acid, sorbic acid etc.

For example, N-octyl, N,N-dipropionic acid, N-benzyl ammonium chloride (20 parts by weight) can be dissolved in phenoxy ethanol (80 parts by weight) and this combination is used for preservation of personal care products (shampoos and body washes with wide range of pH) at 1 to 1.2% level. Challenge test (microbiology) results show that such a combination does a very efficient job of preservation.

Bio-Degradability of Compounds of Formula I:

N-lauryl, N,N-dipropionic acid, N-benzyl ammonium chloride (Formula I, R=$C_{12}$) and for N-octyl, N,N-dipropionic acid, N-benzyl ammonium chloride (Formula I, R=$C_8$) are tested along with some of the popular anionic surfactant like sodium cocoyl glutamate and sodium lauroyl methyl isethionate using OECD protocol (301D). The compounds of Formula I are found to be biodegradable and the ease of bio-degradability has been as good as the anionic surfactants that are employed by the personal care industry, The present invention relates to preservation of personal care products using small dosage (concentration 1 to 2%) of compounds of Formula I. However, the compounds of Formula I can be used at higher dosage for creating hand soap or hand wash formulations that are aimed at good hand hygiene (hand sanitization). Phasing out of Triclosan (due to severe eco-toxicity) from such hand-washes has created a big vacuum for this application. Triclosan is a chlorinated phenolic molecule and other molecule, p-chloro meta xylenol (PCMX) which is being used as replacement of Triclosan in antibacterial soap is also a phenolic and chlorinated molecule. PCMX is a good antimicrobial but it is reported to be toxic to fish and mammals. Overuse of it for hand sanitization can have similar problem like Triclosan. Thus, the need of eco-friendly hand sanitizer-wash can be met with antimicrobial compounds of Formula I that also exhibit good surface active properties necessary for good cleansing (Example 11).

EXAMPLES

Example 1

Synthesis of N-Lauryl, N,N-Dipropionic Acid, N-Benzyl Ammonium Chloride

Step 1. Synthesis of β-Alanine, N-dodecyl-N-(3-methoxy-3-oxopropyl)-, Methyl Ester A mixture of methyl acrylate (86 g, 1000 mmol), lauryl amine (46.3 g, 250 mmol) in methanol (380 mL) was stirred under nitrogen atmosphere at room temperature for 24 h. The excess of methyl acrylate and methanol were removed under reduced pressure using a rotary evaporator to give β-Alanine, N-dodecyl-N-(3-methoxy-3-oxopropyl)-, methyl ester (86.7 g, 97%) as pale yellow viscous oil.

IR: 1739 $cm^{-1}$, 2853 $cm^{-1}$, 2924 $cm^{-1}$

H-NMR (CDCl$_3$): δ 0.9 (t, 3H), δ 1.25 (q, 20H), δ 2.38 (t, 2H), δ 2.45 (t, 4H), δ 2.76 (t, 4H), δ 3.7 (s, 6H)

Step 2. Synthesis of N-Lauryl, N,N-Dimethyldipropionate Benzyl Ammonium Chloride A mixture of a benzyl chloride (13 g, 103 mmol), β-Alanine, N-dodecyl-N-(3-methoxy-3-oxopropyl)-, methyl ester (35.8 g, 100 mmol) in propan-2-ol:water: 3:1 v/v, (70 mL) was stirred at 85-90° C. for 24 h.

Then concentrated the reaction mass to remove Propan-2-ol and water under reduced pressure at 60° C. using a rotary evaporator to give N-Lauryl, N,N-dimethyldipropionate benzyl ammonium chloride (42.5 g, 88%) as pale yellow waxy solid.

IR: 1741 $cm^{-1}$, 2774 $cm^{-1}$, 2850 $cm^{-1}$, 2921 $cm^{-1}$

H-NMR (CDCl$_3$): δ 0.9 (t, 3H), δ 1.25 (q, 20H), δ 2.95 (t, 2H), δ 3.15 (t, 4H), δ 3.37 (t, 4H), δ 3.7 (s, 6H), δ 4.7 (s, 2H), δ 7.3 (t, 5H)

Step 3. Hydrolysis and Acidification of N-Lauryl, N,N-dimethyldipropionate Benzyl Ammonium Chloride to Give N-Lauryl, N,N-Dipropionic Acid Benzyl Ammonium Chloride To a stirred mixture of N-Lauryl, N,N-dimethyldipropionate benzyl ammonium chloride (48.3 g, 100 mmol), and water (72 g), added NaOH 48% solution, (18.3 g, 220 mmol) at room temperature. The reaction mixture was then heated to 85-90° C. for 10-15 h under nitrogen atmosphere.

To a cooled reaction mass, added conc. HCl 35% solution, (22.9 g, 220 mmol) at room temperature. Then phase separated mass at 60-65° C.

The acidified organic mass was then concentrated under reduced pressure at 60° C. using a rotary evaporator to give N-Lauryl, N,N-dipropionic acid benzyl ammonium chloride (43.7 g, 96%) as pale yellow waxy solid.

Physical properties:

| Test Parameters | Results |
| --- | --- |
| Appearance | Yellow Waxy Solid |
| Cationic activity (MW 455) | 95.0 |
| pH (10% dispersion) | 2.5 |
| Solubility in Water, (w/w) at 40° C. | 30% |

-continued

| Test Parameters | Results |
| --- | --- |
| Chloride ion content, % | 7.9 |
| Moisture content, % | 5.2 |
| Melting Point, °C. | 60-65 |
| Acid value, mg/KOH | 245 |
| CMC at 24°C., pH 6.0 mM | 0.38 |

IR: 1722 cm$^{-1}$, 2853 cm$^{-1}$, 2923 cm$^{-1}$
H-NMR (CDCl$_3$): δ 0.9 (t, 3H), δ 1.25 (q, 20H), δ 2.95 (t, 2H), δ 3.15 (t, 4H), δ 3.37 (t, 4H), δ 4.7 (s, 2H), δ 7.3 (t, 5H)

Example 2

Synthesis of N-Octyl, N,N-Dipropionic Acid, N-Benzyl Ammonium Chloride

Step 1. Synthesis of β-Alanine, N-Octyl-N-(3-methoxy-3-oxopropyl)-, Methyl Ester A mixture of methyl acrylate (86 g, 1000 mmol), octyl amine (32.3 g, 250 mmol) in methanol (280 mL) was stirred under nitrogen atmosphere at room temperature for 24 h. The excess of methyl acrylate and methanol were removed under reduced pressure using a rotary evaporator to give β-Alanine, N-octyl-N-(3-methoxy-3-oxopropyl)-, methyl ester (73.8 g, 98%) as pale yellow viscous oil.
IR: 1739 cm$^{-1}$, 2853 cm$^{-1}$, 2924 cm$^{-1}$
H-NMR (CDCl$_3$): δ 0.88 (t, 3H), δ 1.26 (q, 12H), δ 2.39 (t, 2H), δ 2.44 (t, 4H), δ 2.76 (t, 4H), δ 3.66 (s, 6H)

Step 2. Synthesis of N-Octyl, N,N-Dimethyldipropionate N-Benzyl Ammonium Chloride A mixture of a benzyl chloride (13.0 g, 103 mmol), β-Alanine, N-octyl-N-(3-methoxy-3-oxopropyl)-, methyl ester (30.1 g, 100 mmol) in Propan-2-ol:Water: 3:1 v/v, (60 mL) was stirred at 85-90° C. for 24 h.
Then concentrated the reaction mass to remove propan-2-ol and water under reduced pressure at 60° C. using a rotary evaporator to give N-Octyl, N,N-dimethyldipropionate N-benzyl ammonium chloride (36.4 g, 85%) as pale yellow viscous liquid.
IR: 1741 cm$^{-1}$, 2774 cm$^{-1}$, 2850 cm$^{-1}$, 2921 cm$^{-1}$
H-NMR (CDCl$_3$): δ 0.88 (t, 3H), δ 1.26 (q, 12H), δ 2.96 (t, 2H), δ 3.08 (t, 4H), δ 3.29 (t, 4H), δ 3.72 (s, 6H), δ 4.7 (s, 2H), δ 7.45 (t, 5H)

Step 3. Hydrolysis and Acidification of N-Octyl, N,N-Dimethyldipropionate Benzyl Ammonium Chloride to Give N-Octyl, N,N-Dipropionic Acid N-Benzyl Ammonium Chloride To a stirred mixture of N-Octyl, N,N-dimethyldipropionate benzyl ammonium chloride (42.8 g, 100 mmol), and water (64 g), added NaOH 48% solution, (18.3 g, 220 mmol) at room temperature. The reaction mixture was then heated to 85-90° C. for 10-15 h under nitrogen atmosphere.
To a cooled reaction mass, added conc. HCl 35% solution, (22.9 g, 220 mmol) at room temperature. Then phase separated mass at 60-65° C.
The acidified organic mass was then concentrated under reduced pressure at 60° C. using a rotary evaporator to give N-octyl, N,N-dipropionic acid benzyl ammonium chloride (38.3 g, 96%) as pale yellow waxy solid.

Physical properties:

| Test Parameters | Results |
| --- | --- |
| Appearance | Pale yellow translucent viscous liquid |
| Cationic activity (MW 399) | 97.0 |
| pH (10% solution) | 2.4 |
| Solubility in Water, 40% (w/w) at rt. | Soluble |
| Chloride ion content, % | 9.9 |
| Moisture content, % | 2.4 |
| Melting Point, °C. | 40-45 |
| Acid value, mg/KOH | 294 |
| CMC at 24°C., pH 6.0 mM | 2.6 |

IR: 1722 cm$^{-1}$, 2853 cm$^{-1}$, 2923 cm$^{-1}$
H-NMR (CDCl$_3$): δ 0.79 (t, 3H), δ 1.15 (q, 12H), δ 2.92 (t, 2H), δ 3.08 (t, 4H), δ 3.35 (t, 4H), δ 4.7 (s, 2H), δ 7.3 (t, 5H),

Example 3

Synthesis of N-Oleyl, N,N-Dipropionic Acid, N-Benzyl Ammonium Chloride

Step 1. Synthesis of β-Alanine, N-oleyl-N-(3-methoxy-3-oxopropyl)-, Methyl Ester A mixture of methyl acrylate (86 g, 1000 mmol), oleyl amine (66.8 g, 250 mmol) in methanol (280 mL) was stirred under nitrogen atmosphere at room temperature for 24 h. The excess of methyl acrylate and methanol were removed under reduced pressure using a rotary evaporator to give β-Alanine, N-oleyl-N-(3-methoxy-3-oxopropyl)-, methyl ester (106.6 g, 97%) as pale yellow viscous oil.
IR: 1740 cm$^{-1}$, 2853 cm$^{-1}$, 2924 cm$^{-1}$
H-NMR (CDCl$_3$): δ 0.87 (t, 3H), δ 1.25 (m, 24H), δ 2.0 (q, 4H), δ 2.38 (t, 2H), δ 2.44 (t, 4H), δ 2.75 (t, 4H), δ 3.65 (s, 6H), δ 5.34 (t, 2H)

Step 2. Synthesis of N-Oleyl, N,N-Dimethyldipropionate N-Benzyl Ammonium Chloride A mixture of a benzyl chloride (13.0 g, 103 mmol), β-Alanine, N-oleyl-N-(3-methoxy-3-oxopropyl)-, methyl ester (44 g, 100 mmol) in Propan-2-ol:Water: 3:1 v/v, (88 mL) was stirred at 85-90° C. for 24 h.
Then concentrated the reaction mass to remove propan-2-ol and water under reduced pressure at 60° C. using a rotary evaporator to give N-oleyl, N,N-dimethyldipropionate N-benzyl ammonium chloride (48 g, 85%) as pale yellow waxy solid.
IR: 1738 cm$^{-1}$, 2853 cm$^{-1}$, 2924 cm$^{-1}$, 3004 cm$^{-1}$ Step 3. Hydrolysis and Acidification of N-Oleyl, N,N-Dimethyldipropionate Benzyl Ammonium Chloride to Give N-Oleyl, N,N-Dipropionic Acid N-Benzyl Ammonium Chloride To a stirred mixture of N-Oleyl, N,N-dimethyldipropionate benzyl ammonium chloride (56.6 g, 100 mmol), and water (85 g), added NaOH 48% solution, (18.3 g, 220 mmol) at room temperature. The reaction mixture was then heated to 85-90° C. for 10-15 h under nitrogen atmosphere.

To a cooled reaction mass, added conc. HCl 35% solution, (22.9 g, 220 mmol) at room temperature. Then phase separated mass at 60-65° C.

The acidified organic mass was then concentrated under reduced pressure at 60° C. using a rotary evaporator to give N-oleyl, N,N-dipropionic acid benzyl ammonium chloride (51.1 g, 95%) as pale yellow solid.

IR: 1724 cm$^{-1}$, 2853 cm$^{-1}$, 2923 cm$^{-1}$ 3004 cm$^{-1}$

Physical properties:

| Test Parameters | | Results |
|---|---|---|
| Appearance | | Brown waxy solid |
| Cationic activity (MW 537) | | 90.0 |
| pH (10% dispersion) | | 2.5 |
| Solubility in Water, | at rt. | Insoluble |
| 40% (w/w) | at 50° C. | Dispersion but separates on standing |
| Chloride ion content, % | | 8.6 |
| Moisture content, % | | 10.0 |
| Melting Point, ° C. | | 110-120 |
| Acid value, mg/KOH | | 235 |
| CMC at 24° C., pH 6.0 mM | | 0.068 |

Example 4

Preparation of a Body-Wash and its Preservation with N-Octyl, N,N-Dipropionic Acid, N-Benzyl Ammonium Chloride

| Ingredients | % (w/w) |
|---|---|
| Phase A | |
| Water | q.s. to make 100% |
| Sodium Cocoyl Glutamate | 18.7 |
| Sodium Cocoyl Isethionate | |
| Galsoft GLI 21 (P) | |
| Phase B | |
| N-octyl, N,N-dipropionic acid, N-benzyl ammonium chloride | 1.0 |
| Phase C | |
| Citric acid, 50% | |

Procedure:
1. Prepared phase A at 40° C. with stirring.
2. Added phase B to phase A at 40° C. and mix until homogeneous.
3. Cooled to 30° C. with stirring.
4. Adjusted pH to 6.0-7.0 with phase C containing 50% Citric acid solution.

Product Properties:
1. Appearance: Clear liquid
2. Viscosity (cPs), at 25° C., LV 4, rpm 30: 100
3. pH: 6.7

Example 5

Preparation of a Shampoo and its Preservation with N-Octyl, N,N-Dipropionic Acid, N-Benzyl Ammonium Chloride

| Ingredients | % (w/w) |
|---|---|
| Phase A | |
| Water | q.s. to make 100% |
| Sodium laureth 2 EO sulphate | 10.0 |
| Cocoamidopropyl betaine | 16.7 |
| Phase B | |
| N-Octyl, N,N-dipropionic acid, N-benzyl ammonium chloride | 1.0 |
| Phase C | |
| Citric acid, 50% | |

Procedure:
1. Prepared phase A at 40° C. with stirring.
2. Added phase B to phase A at 40° C. and mix until homogeneous.
3. Cooled to 30° C. with stirring.
4. Adjusted pH to 7.0-7.5 with phase C containing 50% Citric acid solution.

Product Properties:
1. Appearance: Clear viscous liquid
2. Viscosity (cPs), at 25° C., LV 4, rpm 30: 1300
3. pH: 7.3

Example 6

Preparation of a Cream and its Preservation with N-Octyl, N,N-Dipropionic Acid, N-Benzyl Ammonium Chloride

| Ingredients | % (w/w) |
|---|---|
| Phase A | |
| Water | q.s. to make 100% |
| Glycerin | 2.0 |
| Laureth-9 | 0.5 |
| PEG-7 Glyceryl Cocoate | 2.0 |
| EDTA disodium salt | 0.05 |
| N-Octyl, N,N-dipropionic acid, N-benzyl ammonium chloride | 1.0 |
| Phase B | |
| Paraffin oil | 4.0 |
| Stearic acid | 2.0 |
| Glycerol monostearate | 7.0 |
| Cetostearyl alcohol | 6.0 |
| Isopropyl palmitate | 5.0 |
| Phase C | |
| Caustic lye, 48% | |

Procedure:
1. Mixed phase A and phase B ingredients in separate vessels at 60-65° C.
2. Added phase B to phase A and emulsify at 60-65° C. by using Silverson Homogenizer until homogeneous emulsion is observed
3. Cooled to 30° C. with gentle stirring.

4. Adjusted the pH to 5.5-6.5 with phase C containing 48% Caustic lye solution.

Product properties:
1. Appearance: White cream
2. pH (10% dispersion): 5.9

Example 7

Preparation of a Body Wash and its Preservation with N-Lauryl, N,N-Dipropionic Acid, N-Benzyl Ammonium Chloride

| Ingredients | % (w/w) |
|---|---|
| Phase A | |
| Water | q.s. to make 100% |
| Sodium Cocoyl Glutamate | 18.7 |
| Sodium Cocoyl Isethionate | |
| Galsoft GLI 21 (P) | |
| Phase B | |
| N-lauryl, N,N-dipropionic acid, N-benzyl ammonium chloride | 2.0 |
| Phase C | |
| Citric acid, 50% | |

Procedure:
1. Prepared phase A at 40° C. with stirring.
2. Added phase B to phase A at 40° C. and mixed until homogeneous.
3. Cooled to 30° C. with stirring.
4. Adjusted pH to 6.0-7.0 with phase C containing 50% Citric acid solution.

Product Properties:
1. Appearance: Clear liquid
2. Viscosity (cPs), at 25° C., LV 4, rpm 30: 100
3. pH: 6.7

Example 8

Preparation of a Shampoo and its Preservation with N-Lauryl, N,N-Dipropionic Acid, N-Benzyl Ammonium Chloride

| Ingredients | % (w/w) |
|---|---|
| Phase A | |
| Water | q.s. to make 100% |
| Sodium laureth 2 EO sulphate | 10.0 |
| Cocoamidopropyl betaine | 16.7 |
| Phase B | |
| N-lauryl, N,N-dipropionic acid, N-benzyl ammonium chloride | 2.0 |
| Phase C | |
| Citric acid, 50% | |

Procedure:
1. Prepared phase A at 40° C. with stirring.
2. Added phase B to phase A at 40° C. and mixed until homogeneous.
3. Cooled to 30° C. with stirring.
4. Adjusted pH to 7.0-7.5 with phase C containing 50% Citric acid solution.

Product Properties:
1. Appearance: Clear viscous liquid
2. Viscosity (cPs), at 25° C., LV 4, rpm 12: 4000
3. pH: 7.3

Example 9

Preparation of a Cream and its Preservation with N-Lauryl, N,N-Dipropionic Acid, N-Benzyl Ammonium Chloride

| Ingredients | % (w/w) |
|---|---|
| Phase A | |
| Water | q.s. to make 100% |
| Glycerin | 2.0 |
| Laureth-9 | 0.5 |
| PEG-7 Glyceryl Cocoate | 2.0 |
| EDTA disodium salt | 0.05 |
| N-Lauryl, N,N-dipropionic acid, N-benzyl ammonium chloride | 1.0 |
| Phase B | |
| Paraffin oil | 4.0 |
| Stearic acid | 2.0 |
| Glycerol monostearate | 7.0 |
| Cetostearyl alcohol | 6.0 |
| Isopropyl palmitate | 5.0 |
| Phase C | |
| Caustic lye, 48% | |

Procedure:
1. Mixed phase A and phase B ingredients in separate vessels at 60-65° C.
2. Added phase B to phase A and emulsify at 60-65° C. by using Silverson Homogenizer until homogeneous emulsion is observed
3. Cooled to 30° C. with gentle stirring.
4. Adjusted the pH to 5.5-6.5 with phase C consisting 48% Caustic lye solution.

Product Properties:
1. Appearance: White cream
2. pH (10% dispersion): 5.9

Example 10

Preparation of a Hand Dish-Wash and its Preservation with N-Lauryl, N,N-Dipropionic Acid, N-Benzyl Ammonium Chloride

| Ingredients | % (w/w) |
|---|---|
| Phase A | |
| Water | q.s. to make 100% |
| Sodium Gluconate | 0.3 |
| Sodium Carbonate | 0.3 |
| Phase B | |
| Caprylyl/Myristyl glucoside | 1.5 |
| Lauramine Oxide (30%) | 1.4 |
| N-Lauryl, N,N-dipropionic acid, N-benzyl ammonium chloride | 2.0 |
| Phase C | |
| Caustic lye, 48% | |

Procedure:
1. Mixed phase A ingredients until homogeneous at 40-45° C.
2. Then added phase B at 40-45° C. and mixed until homogeneous.
3. Cooled to room temperature.
4. Adjusted the pH to 9.0-10.0 with phase C containing 48% Caustic lye solution.

Product properties:
1. Appearance: Clear liquid
2. pH (as such): 9.5

The above formulations (Example 4, 5, 6, 7, 8, 9 & 10) pass the challenge test performed according to PCPC protocol using *Escherichia coli* ATCC 8739, *Pseudomonas aeruginosa* ATCC 15442 (Gram –ve bacteria), *Staphylococcus aureus* ATCC 6538, *Propionibacterium acnes* MTCC 1951, (Gram +ve) *Candida albicans* ATCC 10231, *Malassezia furfur* MTCC 1374 (yeast) and *Aspergillus niger* ATCC 16404 (mold).

Example 11

Preparation of an Anti-Bacterial Hand Wash with N-Octyl, N,N-Dipropionic Acid, N-Benzyl Ammonium Chloride

| Ingredients | % (w/w) |
|---|---|
| Phase A | |
| Water | q.s. to make 100% |
| Sodium laureth sulfate 2 EO | 17.1 |
| Phase B | |
| Ethylene glycol distearate | 2.0 |
| Cocomonoethanol amide | 1.0 |
| Phase C | |
| N-Octyl, N,N-dipropionic acid, N-benzyl ammonium chloride | 5.0 |
| Phase D | |
| Glycerin | 1.0 |
| Propylene glycol | 1.0 |
| Tetrasodium EDTA | 0.1 |
| Sodium chloride | 1.1 |
| Phase E | |
| Caustic lye, 48% | |

Procedure:
1. Mixed phase A ingredients and heated to 70-75° C.
2. Added phase B at 70-75° C. and mixed until homogeneous.
3. Cooled to 45° C. and added phase C. Stirred for 15 min.
4. Cooled to rt and added phase D.
5. Adjusted pH to 4.0 with phase E containing 48% Caustic lye solution.

Product properties:
1. Appearance: Pearly viscous liquid
2. pH (as such): 4.0
3. Solids, %: 21.0
4. Anionic activity (MW 384), %: 12.1
5. Viscosity at 25° C., LV 4, rpm 12, cP: 8000
6. Sodium chloride, %: 1.2
7. Foam volume by Hart de-George method: 210 Hardness of water 150 ppm, mL Example 12 (Comparative Example)

Preparation of a Shampoo and its Preservation with Benzalkonium Chloride

| Ingredients | % (w/w) |
|---|---|
| Phase A | |
| Water | q.s. to make 100% |
| Sodium laureth 2 EO sulphate | 10.0 |
| Cocoamidopropyl betaine | 16.7 |
| Phase B | |
| Benzalkonium chloride | 1.0 |
| Phase C | |
| Citric acid, 50% | |

Procedure:
1. Prepared phase A at 40° C. with stirring.
2. Added phase B to phase A at 40° C. and mixed until homogeneous.
3. Cooled to 30° C. with stirring.
4. Adjusted pH to 7.0-7.5 with phase C containing 50% Citric acid solution.

Product properties:
1. Appearance: Clear viscous liquid
2. Viscosity (cPs), at 25° C., LV 4, rpm 30: 1200
3. pH 7.2

The above formulation did not pass the challenge test performed according to PCPC protocol using *Escherichia coli* ATCC 8739, *Pseudomonas aeruginosa* ATCC 15442 (Gram –ve bacteria), *Staphylococcus aureus* ATCC 6538, *Propionibacterium acnes* ATCC 1951, (Gram +ve) *Candida albicans* ATCC 10231, *Malassezia furfur* ATCC 1374 (yeast) and *Aspergaus niger* ATCC 16404 (mold).

Advantages of the Invention

The advantages of N-Alkyl, N,N-dipropionic acid, benzyl ammonium chlorides, of Formula I (R=$C_8$ to $C_{18}$) are as follows:

1) The compounds of Formula I (R=$C_8$ to $C_{18}$) do not contain any structural feature such as phenolic moiety, halogens or any formaldehyde releasing functionality that would get associated with cytotoxic effects.
2) The compounds of Formula I (R=$C_8$ to $C_{18}$) exhibit broad spectrum of antimicrobial activity covering bacteria, yeast and mold and hence these are useful as 'stand-alone' preservatives in personal care products.
3) As explained in the background that the arsenal of effective yet non-toxic antimicrobials has shrunk significantly to a very few molecules with 'limited antimicrobial activity' like phenoxy ethanol, benzoic acid, dehydroacetic acid, carpyloyl glycine and undecylenoyl glycine etc. In view of this fact, addition of compounds of Formula I to the current limited arsenal available opens up several options of synergistic combinations for combinatorial approach for preservation. This approach is explained in 'detailed discussion section' where a compound of Formula I is used in combination with phenoxy ethanol.
4) The compounds of Formula I of this invention show excellent activity against fungus. They exhibit good preservation property against fungus *A. niger* in the presence of anionic surfactants not only in acidic pH but in alkaline pH as well. It is worth noting that there are no non-toxic antimicrobials available currently that can take care of fungi at alkaline pH.

5) The compounds of Formula I (R=$C_8$ to $C_{18}$) exhibit active antimicrobial preservative property in the presence of anionic surfactants. Almost all home care and personal care formulations deploy anionic surfactants for their either detergent (cleansing) or emulsifying action.

6) The compounds of Formula I (R=$C_8$ to $C_{18}$) are surface active as well as they exhibit good antimicrobial properties. This makes them suitable for antibacterial handwash or hand-hygiene wash. Surface active properties take care of cleansing the surface of dirt and sebum and antibacterial properties take care of the resident flora on the hands.

The compound of Formula I are bio-degradable and hence can be used for preservation of home and personal care products as well as for the sanitization of hands or other inanimate surfaces.

We claim:

1. An N-Alkyl-N,N-bis(2-carboxyethyl)-N-benzyl ammonium chloride of Formula I,

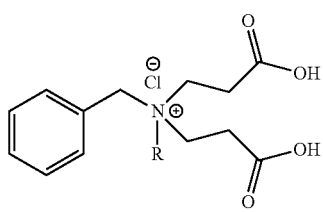

Formula I wherein R is selected from the group consisting of C8 to C18 saturated or unsaturated alkyl chains, as an antimicrobial preservative for home and personal care compositions.

2. The N-Alkyl-N,N-bis(2-carboxyethyl)-N-benzyl ammonium chloride of Formula I as claimed in claim 1, selected from the group consisting of;
   a) N-Lauryl-N,N-bis(2-carboxyethyl)-N-benzyl ammonium chloride;
   b) N-Octyl-N,N-bis(2-carboxyethyl)-N-benzyl ammonium chloride;
   c) N-Oleyl-N,N-bis(2-carboxyethyl)-N-benzyl ammonium chloride; and
   d) mixtures thereof.

3. A process for synthesis of the N-Alkyl-N,N-bis(2-carboxyethyl)-N-benzyl ammonium chloride of Formula I as claimed in claim 1, the process comprising;

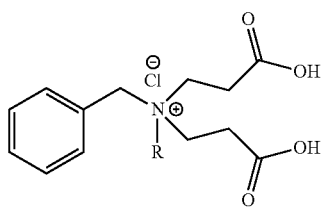

Formula I

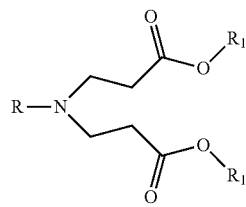

Formula II

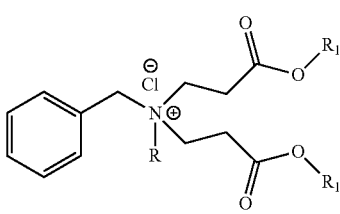

Formula III a) reacting a primary alkyl amine of formula $RNH_2$, wherein R is selected from the group consisting of C8 to C18 saturated or unsaturated alkyl chains, with an alkyl acrylate to form a Michael adduct of Formula II, where $R_1$ is an alkyl group;
b) quaternizing the Michael adduct of Formula II with benzyl chloride to form a compound of Formula III; and
c) hydrolyzing the compound of Formula III in the presence of alkali, followed by acidification to obtain the the N-Alkyl-N,N-bis(2-carboxyethyl)-N-benzyl ammonium chloride of Formula I.

4. A process for synthesis of the N-Alkyl-N,N-bis(2-carboxyethyl)-N-benzyl ammonium chloride of Formula I as claimed in claim 1, the process comprising;

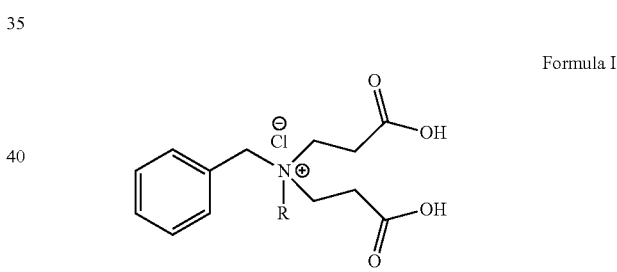

Formula I

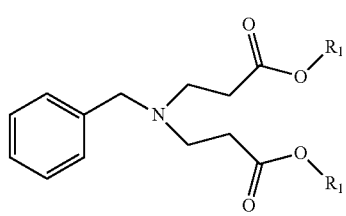

Formula II

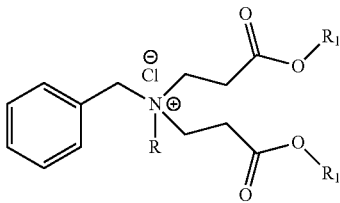

Formula III a) reacting benzyl amine with an alkyl acrylate to form a Michael adduct of Formula II, where $R_1$ is an alkyl group;
b) quaternizing the Michael adduct of Formula II with a primary alkyl amine of formula $RNH_2$, wherein R is selected from the group consisting of C8 to C18 saturated or unsaturated alkyl chains, to form a compound of Formula III; and c) hydrolyzing the compound of Formula III with alkali, followed by acidification followed to obtain the compound of formula I.

5. The method of claim 3, wherein the alkyl acrylate is ethyl acrylate or methyl acrylate.

6. The method of claim 4, wherein the alkyl acrylate is ethyl acrylate or methyl acrylate.

7. A personal care formulation, comprising:

an effective amount of the N-Alkyl-N,N-bis(2-carboxyethyl)-N-benzyl ammonium chloride of Formula I as claimed in claim 1 as an antimicrobial agent; and at least one additional ingredient.

8. The personal care formulation of claim 7, wherein the additional ingredient is selected from the group consisting of anionic surfactants, amphoteric surfactants, non-ionic surfactants, pearlizers, emollients, anti-inflammatory agents, anti-microbial preservatives, UV absorbers, UV blockers, synthetic and/or natural polymeric conditioners, silicones, gums, rheology modifiers, vegetable oils, film formers, vitamins, protein derivatives, anti-acne agents, anti-dandruff agents, moisturizers, humectants, botanicals, emulsifiers, and mixtures thereof.

9. The personal care formulation of claim 7, wherein the antimicrobial personal care formulation comprises the N-Alkyl-N,N-bis(2-carboxyethyl)-N-benzyl ammonium chloride of Formula I in an amount of at least 0.3% by weight of the personal care formulation.

10. A home care formulation, comprising:

an effective amount of the N-Alkyl-N,N-bis(2-carboxyethyl)-N-benzyl ammonium chloride of Formula I as claimed in claim 1 as an antimicrobial agent; and at least one additional ingredient.

11. The home care formulation of claim 10, wherein the additional ingredient is selected from the group consisting of anionic surfactants, cationic surfactants, amphoteric surfactants, polymers, rheology modifiers, pearlizers, urea, hydrotropes, polyalkylene glycols, chelating agents, and mixtures thereof.

12. The home care formulation of claim 10, wherein the antimicrobial personal care formulation comprises the N-Alkyl-N,N-bis(2-carboxyethyl)-N-benzyl ammonium chloride of Formula I in an amount of at least 0.3% by weight of the home care formulation.

* * * * *